(12) United States Patent
Nathanson et al.

(10) Patent No.: US 9,415,203 B2
(45) Date of Patent: *Aug. 16, 2016

(54) ELECTROSTIMULATION DEVICES

(71) Applicant: CACI Microlift Limited, Hertfordshire (GB)

(72) Inventors: Dean Nathanson, Edgware (GB); Shilen Thakker, Hertfordshire (GB)

(73) Assignee: CACI Microlift Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/150,367

(22) Filed: Jan. 8, 2014

(65) Prior Publication Data
US 2014/0121572 A1 May 1, 2014

Related U.S. Application Data

(63) Continuation-in-part of application No. 12/870,361, filed on Aug. 27, 2010, now Pat. No. 8,639,361.

(30) Foreign Application Priority Data

Aug. 28, 2009 (GB) .................................. 0914981.6

(51) Int. Cl.
*A61N 1/00* (2006.01)
*A61N 1/04* (2006.01)
*A61N 1/32* (2006.01)

(52) U.S. Cl.
CPC .............. *A61N 1/0452* (2013.01); *A61N 1/322* (2013.01); *A61N 1/328* (2013.01); *A61N 1/044* (2013.01); *A61N 1/0448* (2013.01); *A61N 1/325* (2013.01)

(58) Field of Classification Search
CPC ..... A61N 1/26; A61N 1/0424; A61N 1/0428; A61N 1/0452; A61N 1/18
See application file for complete search history.

(56) References Cited

U.S. PATENT DOCUMENTS 4,180,079 A 12/1979 Wing
4,745,420 A 5/1988 Gerstenmaier
(Continued)

FOREIGN PATENT DOCUMENTS

EP 0387176 A1 9/1990
EP 0603451 A1 6/1994
(Continued)

OTHER PUBLICATIONS

Cheng et al., "The Effects of Electric Currents on ATP Generation, Protein Synthesis, and Membrane Transport in Rat Skin", Clin. Orthop. Relat. Res., 1982, pp. 264-272, Nov.-Dec.(171).
(Continued)

*Primary Examiner* — Scott Getzow
(74) *Attorney, Agent, or Firm* — Emily A. Shouse; Patterson Intellectual Property Law PC

(57) ABSTRACT

A hand held electrostimulation device has a handle having a first side member and a second side member. At least one first electrode is provided on the first side member and at least one second electrode is provided on the second side member. The handle is configured so that a user can cause relative movement of the first and second side members from a rest position and is resiliently biased to return to the rest position to cause relative movement of the first and second electrodes to massage skin engaged by the electrodes while applying electricity to said skin via said electrodes.

22 Claims, 8 Drawing Sheets

(56) References Cited

U.S. PATENT DOCUMENTS

| | | | |
|---|---|---|---|
| 4,957,480 A | 9/1990 | Morenings | |
| 5,318,514 A | 6/1994 | Hofmann | |
| 5,688,233 A | 11/1997 | Hofmann et al. | |
| 5,702,035 A | 12/1997 | Tsao | |
| 6,249,706 B1 | 6/2001 | Sobota et al. | |
| 6,341,237 B1 | 1/2002 | Hurtado | |
| 6,389,319 B1 | 5/2002 | Lee | |
| 6,477,410 B1 * | 11/2002 | Henley et al. | 604/20 |
| 6,801,808 B2 | 10/2004 | Lee | |
| 7,018,345 B2 | 3/2006 | Mori et al. | |
| 7,340,309 B2 | 3/2008 | Miazga et al. | |
| 2005/0234516 A1 | 10/2005 | Gueret | |
| 2008/0027508 A1 | 1/2008 | Chu | |
| 2008/0195181 A1 | 8/2008 | Cole | |
| 2009/0093749 A1 | 4/2009 | Shalev et al. | |

FOREIGN PATENT DOCUMENTS

| | | |
|---|---|---|
| FR | 2256750 | 8/1975 |
| GB | 2148717 A | 6/1985 |
| JP | 3162870 A | 7/1991 |
| JP | 7116267 A | 5/1995 |
| JP | 2004129928 A | 4/2004 |
| WO | 0191849 A1 | 12/2001 |
| WO | 2006116728 A2 | 11/2006 |

OTHER PUBLICATIONS

UK Application Search Report in Application No. GB1014274.3 dated Oct. 28, 2010. (not prior art).

European Search Report in EP 10 17 4299 dated Dec. 16, 2010. (not prior art).

* cited by examiner

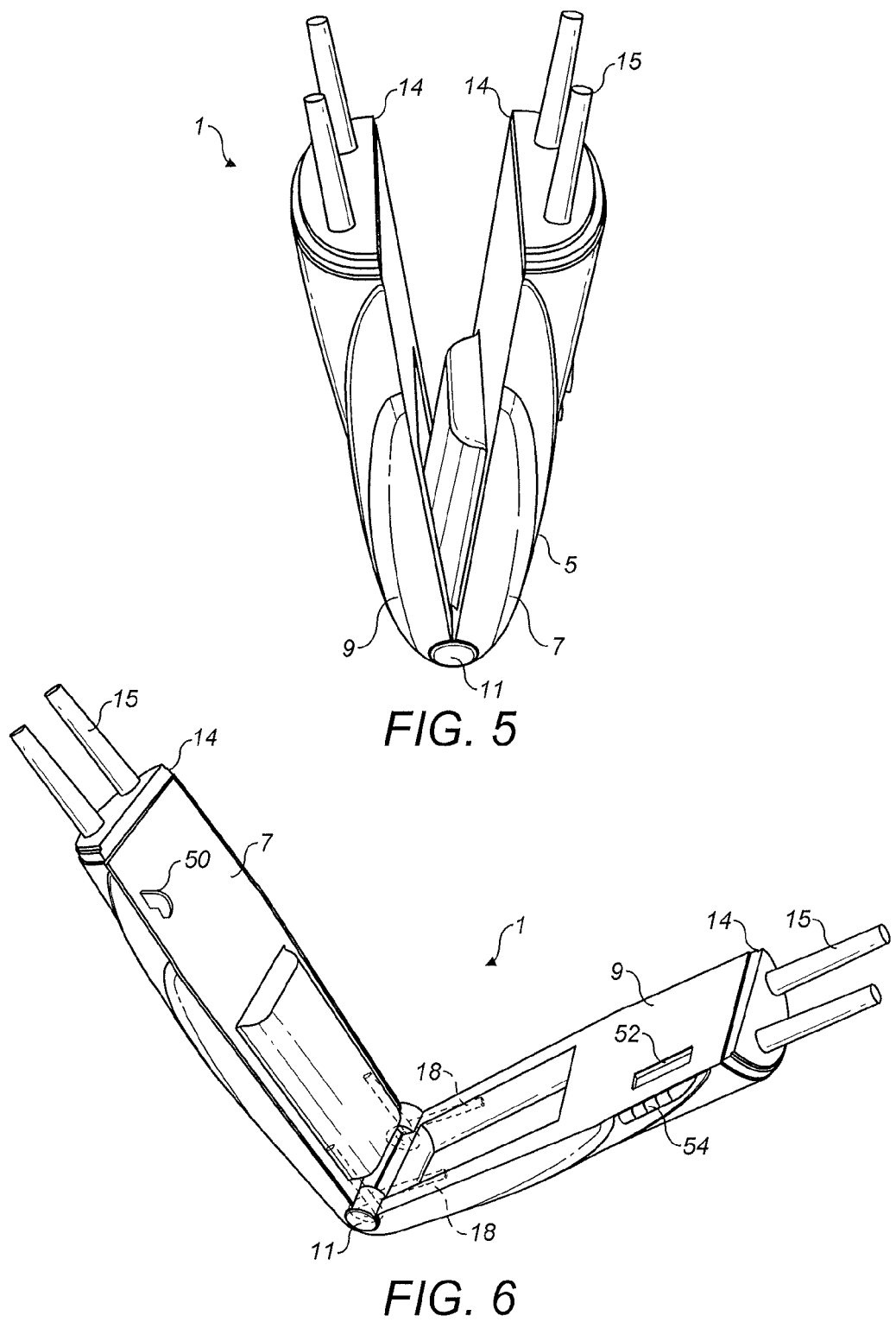

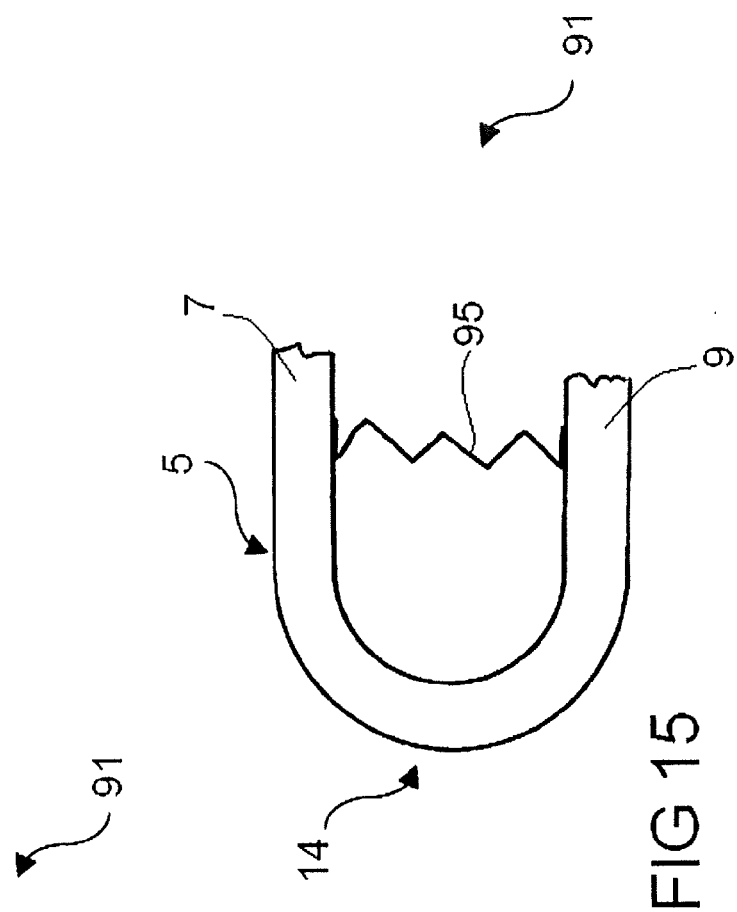
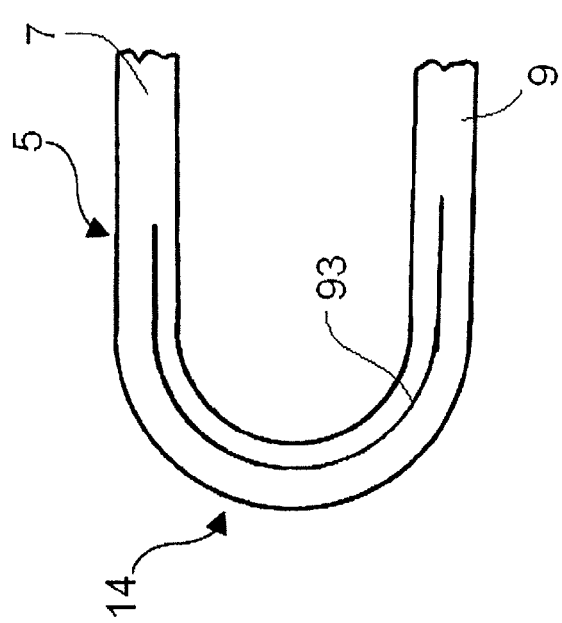

ELECTROSTIMULATION DEVICES

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

CROSS-REFERENCES TO RELATED APPLICATIONS

This application claims benefit of the following patent application(s) which is/are hereby incorporated by reference: GB 0914981.6 filed Aug. 28, 2009 and U.S. Ser. No. 12/870,361 filed Aug. 27, 2010.

BACKGROUND OF THE INVENTION

This invention relates to electrostimulation devices and particularly, but not exclusively to microcurrent electrostimulation devices that are suitable for applying currents in the order of $10^{-6}$ amperes to the skin and underlying muscle of a user.

Previously proposed electrostimulation devices have tended to be of one of two types—microcurrent devices that are configured to apply currents in the order of $10^{-6}$ amperes to the skin and underlying muscle of a user and millicurrent devices that are configured to apply larger currents of in the order of $10^{-3}$ amperes to the skin and underlying muscles of a user.

In general terms, millicurrent devices are designed to stimulate muscle tissue and improve muscle tone by virtue of a process known as "passive gymnastics" where a current applied to the skin and underlying muscle of a subject causes an involuntary rhythmic contraction of the muscles that improves muscle tone. Microcurrent devices are configured to apply much smaller currents. Treatments with a microcurrent device do not cause muscle contraction and tend to be barely detectable by the subject.

Microcurrent treatments have been shown to increase the amount of ATP (adenosine triphosphate) within the cells of a muscle. For example, a study by Ngok Cheng, M.D. et al ("The Effects of Electric Currents on ATP Generation, Protein Synthesis, and Membrane Transport in Rat Skin," Clinical Orthopaedics and Related Research, No. 171, November-December 1982, pp. 264-271) showed that the application of a current of in the order of 50 to 500 microamperes to the skin and underlying muscle of a subject causes an increase in mitochondria and protein synthesis in the muscle, an increase in aminoisobutyric acid uptake, an increase in protein synthesis and Gluconeogenesis (biosynthesis of new glucose) and a 300-500% increase in ATP (Adenosine triphosphate) levels.

These dramatic increases in cellular ATP levels have been shown to help muscles retain a re-educated form for longer periods of time, and as a consequence such techniques are of use in muscle toning treatments. However, for these benefits to be appreciable it is necessary to for the muscle to be manipulated (for example by extending or compressing the muscle) whilst the treatment is taking place. In a salon environment this is relatively easy to accomplish as microcurrent electrostimulation devices typically comprise a pair of probes that can be used by a technician during a treatment to manipulate the skin and muscle so that the muscle is forced into a desired form for re-education. This contrasts with the home environment where subjects typically apply microcurrent treatments to themselves without the assistance of another person.

One previously proposed microcurrent electrostimulation device that is intended for personal rather than commercial use is the Rio® facial rejuvenator device offered for sale by The Dezac Group Ltd. This device is similar to commercial devices in that it comprises a pair of wands with conducting tips that can be used to squeeze the skin and underlying muscle whilst a microcurrent is applied thereto. Whilst this device does allow a subject to manipulate their skin and underlying muscle in the course of a muscle toning electrostimulation treatment, a problem with the device is that the subject needs to look in a mirror to be able to locate the wands on the skin and squeeze or lengthen the correct muscle.

Another previously proposed electrostimulation device is the NuFace® device from the Carol Cole Company (see WO2006/116728). This device comprises a hand-holdable housing from which a pair of electrodes project and circuitry for establishing a potential difference between the electrodes so that a microcurrent flows between the electrodes when the electrodes are placed on the skin.

A drawback with the NuFace® device is that as it can only be used in a manner in which the electrodes are brushed over the skin. It cannot be used for muscle toning treatments where the skin and muscle are manipulated whilst the current is applied. As aforementioned, for electrostimulation treatments that are designed to re-educate muscles (for example a cosmetic treatment to reduce the severity of wrinkles) it is preferred that the muscle be manipulated (for example squeezed or lengthened) whilst the treatment is undertaken so that the increased cellular levels of ATP can retain the muscle in its re-educated form for longer.

Another previously proposed device is the Tua Viso electrostimulation device from Vupiesse Italia (see EP 0603 451). This device is similar in concept to the NuFace® device and is used in the same way by brushing the electrodes over the surface of the skin to be treated. As a consequence, the Tua Viso device suffers from the same drawbacks as the NuFace® device. A further problem is that whilst the Tua Viso device is described as being a microcurrent device, tests have indicated that it actually applies a current that is closer to that a millicurrent device would produce.

Since research has shown that the application of a current of 600 micro amps or more can actually reduce cellular ATP levels, the Tua Viso device would not be suitable for enhancing retention of re-educated muscle form in the manner aforementioned. Also the application of currents of this magnitude to delicate facial muscles can be uncomfortable, and that the characteristic muscle contractions associated with these higher current devices can actually worsen the appearance of lines and wrinkles in some areas of the face.

Iontophoresis is a known process in which charged particles are propelled, non-invasively, through the dermis of a subject by means of a repulsive electromotive force that results from the application of an electric field to a similarly charged particle (such as the particles of a medicament or a cosmetic treatment). The applied electric field pushes the particles deeper into the skin to achieve a better therapeutic or cosmetic effect.

In the context of electrostimulation devices it has previously been proposed to provide electrolytic fluids that function to improve current flow to the skin of the subject, and for these fluids to have a cosmetic or therapeutic effect. For example, in the context of the NuFace® device, it has been proposed to provide a conductivity gel that is smeared over the subject's face prior to use of the device, and an optimizing mist that can be sprayed onto the gel to keep the gel moist during a NuFace® treatment. Smearing a subject's face with gel is necessarily quite messy and it is difficult to ensure that the gel is exactly where it is needed. Also cleaning the device after use can be problematic.

The Tua Viso device has chambers that are associated with each of the electrodes, and which can be filled with fluid or fluid-filled cartridges that are sealed with a breakable membrane. It is known to cover each of the electrodes of the Tua Viso device with a "spongey material" that is humidified by the fluid to keep the skin dampened during use of the device. Whilst this arrangement is better than that proposed for the NuFace® device, the electrode assemblies of the Tua Viso device still need to be disassembled to be properly cleaned after use. The sponges can also be difficult to put on and take off, and that the need to purchase replacement cartridges and sponges can substantially increase the cost of using of the device.

BRIEF SUMMARY OF THE INVENTION

The invention provides a hand held electrostimulation device comprising: a housing comprising a first housing part and a second housing part; at least one first electrode carried by said first housing part and at least one second electrode carried by said second housing part, and a controller to control a supply of electricity to said electrodes, wherein said first and second electrodes are spaced apart and said spacing is adjustable by relative movement of said first and second housing parts.

The invention also includes a method of cosmetic treatment of human skin using a hand held electrostimulation device comprising: applying at least one first electrode carried by a first housing part of said device and at least one second electrode carried by a second housing part of said device to said skin; applying an electrical current to said skin via said electrodes; and manipulating said skin by relative movement of said first and second electrodes caused by relative movement of said first and second housing parts that causes a spacing between said at least one first electrode and said at least one second electrode to change.

The invention also includes a hand held electrostimulation device comprising: a first housing member and a second housing member hinge connected to said first housing member to permit relative movement between said housing members; at least one first electrode carried by said first housing member; at least one second electrode carried by said second housing member; a control element to control a supply of electrical current to said electrodes; and at least one biasing member to bias said first and second housing members to a predetermined rest position that defines a first spacing between said at least one first electrode and said at least one second electrode, said spacing being changed by relative movement of said first and second housing members against said at least one biasing member to a non-rest position at which said at least one biasing member operates to return said first and second housing members to said rest position to assist in a muscle manipulation activity.

The invention also includes a hand held electrostimulation device comprising a casing carrying a first electrode, a second electrode and a control device to control a supply of electricity to said first and second electrodes, at least one of said first and second electrodes being movable to permit a spacing between said electrodes to be varied and at least one of said first and second electrodes being provided with a holder for a removable fluid-filled applicator whereby fluid from a said fluid-filled applicator held in a said holder and electricity from said first and second electrodes can be at least substantially simultaneously applied to skin of a user.

The invention also includes a method of treatment of human skin using a hand held electrostimulation device that comprises a casing that supports a first electrode and a second electrode such that a spacing between said electrodes can be varied, at least one of said electrodes being provided with a holder for a fluid-filled applicator, said method comprising: loading a fluid-filled applicator to said holder; supplying an electrical current to said electrodes; and applying said electrostimulation device to said skin such that electricity from said electrodes and fluid from said fluid filled applicator are applied at least substantially simultaneously to said skin.

The invention also includes an electrostimulation device comprising: a hand-holdable housing; first and second electrodes; a control interface that is user operable to couple a source of electricity to said electrodes; and a holder for a fluid-bearing cotton bud; the device being configured to enable fluid from said cotton bud to be applied to skin of a user as electricity is supplied to said skin.

BRIEF DESCRIPTION OF THE SEVERAL VIEWS OF THE DRAWINGS

In order that the invention may be well understood, some embodiments thereof, which are given by way of example only, will now be described with reference to the drawings, in which:

FIG. 5 shows one operating condition of the device;

FIG. 6 shows another operating condition of the device;

FIG. 14 is a schematic partial side view illustrating an optional biasing element that may be included in the device of FIG. 13;

FIG. 15 is a schematic partial side view illustrating another optional biasing element that may be included in the device of FIG. 13.

DETAILED DESCRIPTION OF THE INVENTION

Figure 1:
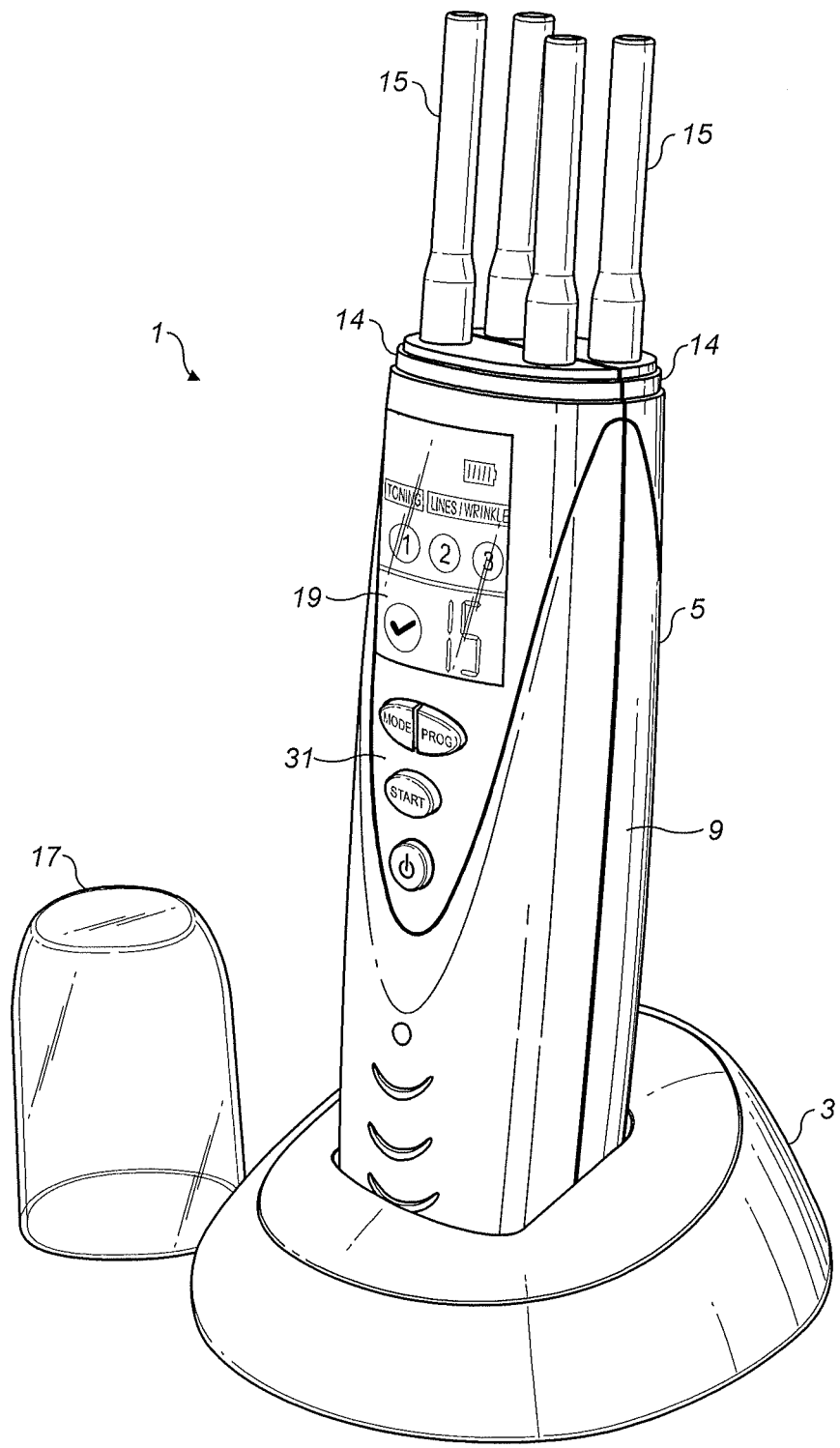
FIG. 1 is a perspective view of a first example of a hand held electrostimulation device.
Figure 2:
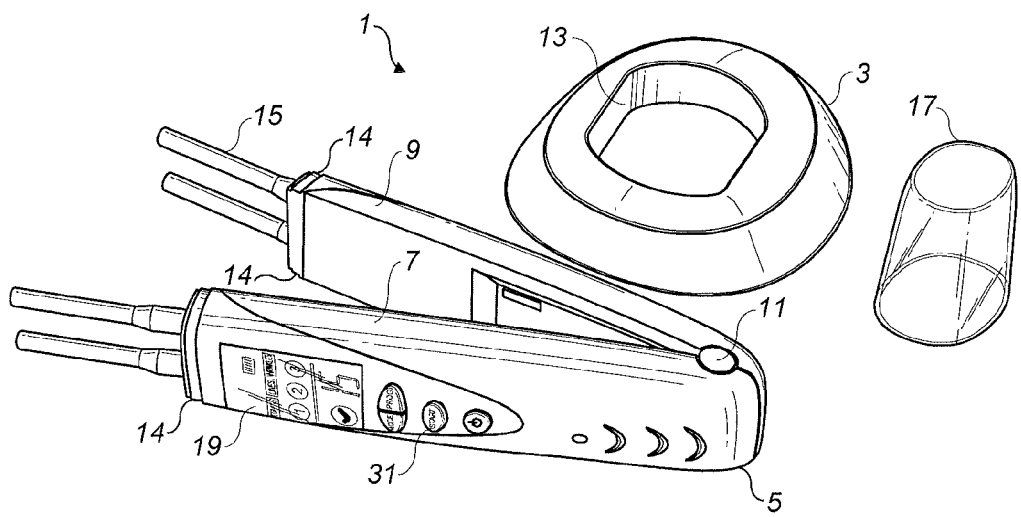
FIG. 2 is a perspective view of the device of FIG. 1.

FIGS. 1 and 2 show a hand held electrostimulation device 1 with a charging cradle 3. The device 1 comprises a hand-holdable housing 5 that is configured to fit in the hand of a normal adult user for one-handed operation. The housing 5 comprises a first housing part 7 and a second housing part 9 that are joined to one another by a hinge 11 disposed at one end region of the device. The hinge 11 forms a pivot axis about which the first and second parts 7, 9 can move relative to one another.

The charging cradle 3 is configured to be plugged into a mains power outlet (not shown) and includes a socket 13. The socket 13 is shaped to receive the end region of the device at which the hinge 11 is disposed. The socket 13 includes a plurality of electrical connectors (not shown) that are capable of coupling with connectors (not shown) in the device 1 when the device is supported in the cradle 3 to enable a battery in the device 1 to be recharged. Suitable electrical connectors and charging stations for hand held devices will be known to those skilled in the art and will, therefore, not be described in detail herein. It will be understood that it is not essential that battery charging is by way of contact technology and that the cradle 3 and device 1 may be equipped for non-contact charging by, for example, an inductive charging system.

As shown in FIGS. 1 and 2, the respective ends of the first and second housing parts 7, 9 distal from the hinge 11 have at least one electrode 15 (in this particular example two electrodes) projecting therefrom. The electrodes 15 are to supply electrical energy to the skin and muscle of a user, particularly but not exclusively to facial skin and muscle.

The device 1 may be provided with a cap 17 that can be fitted over the electrodes 15 when the device 1 is in a fully closed position (shown in FIG. 1) to keep the electrodes clean. In one envisaged example a locking mechanism may be provided to keep the device in the fully closed position. Such a locking mechanism may also be used to keep the device in a fully closed condition when the device is to be operated in a lines/wrinkles mode where muscle manipulation is not required. In the example illustrated in FIG. 6, the locking mechanism comprises a hook-like projection 50 provided on the first housing part 7 that can be received in a suitable recess 52 provided in the second housing part 9 and a locking member (not visible) within the second housing part that can be slid into locking engagement with the projection 50 by means of a slider 54 provided in a recess on a side surface of the second housing part. In another envisaged implementation, fitting the cap 17 over the electrodes 15 may be sufficient to keep the device in its fully closed condition.

The device 1 may be provided resilient biasing members 18 that are arranged to urge the first and second housing parts 7, 9 away from one another to the rest position shown in FIGS. 2 and 5. In the illustrated example, the resilient biasing members are torsion springs that are mounted on the hinge axis. Each torsion spring has two arms that are secured in respective recesses provided in the first and second housing parts 7, 9. In the rest position, the ends 14 of the first and second housing parts 7, 9 are slightly spaced from one another. As illustrated by FIG. 6, the ends 14 of the first and second housing parts 7, 9 can be moved against the biasing members 18 to increase the spacing between the electrodes 15 and as illustrated by FIG. 1, the housing parts can be brought together against the biasing members to reduce the spacing between the electrodes.

The biasing force provided by the biasing members 18 can assist the user in manipulating skin tissue by stretching or compressing a muscle while electrical current is applied to the skin. For example if the user wishes to manipulate skin tissue by compressing a muscle, the user can move the housing parts 7, 9 from the rest position shown in FIG. 5 to a more open position in which the spacing between the electrodes 15 is increased and once the electrodes are placed against the skin, allow the biasing members to move the electrodes towards one another by simply relaxing their grip on the housing 5. Similarly, when the user wishes to stretch a muscle, the electrodes 15 can be placed against the skin with the device 1 in the fully closed position shown in FIG. 1 and the biasing members 18 then allowed to urge the electrodes apart by the user simply relaxing their grip on the housing 5. This is advantageous as the skin and muscle should be manipulated whilst being electrically stimulated if the muscle is to retain its re-educated form for longer.

Figure 3:
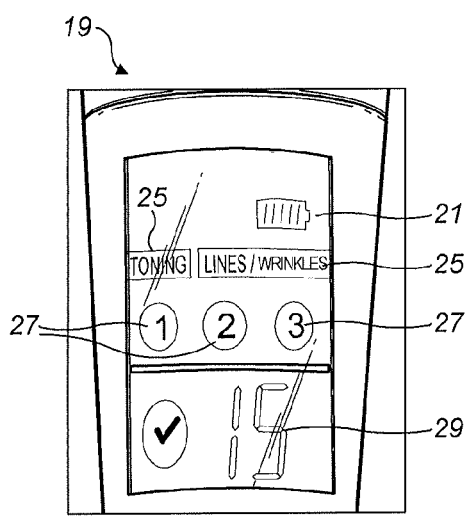
FIG. 3 is a schematic representation of a display of the device.

Referring now to FIG. 3, the first part 7 of the housing 5 includes a display screen 19 to display various items of information to the user of the device. The screen 19 includes an icon 21 which indicates the state of charge of a battery contained within the device (which battery can preferably be recharged by means of the charging cradle 3). The screen 19 also provides a visual indication of a selected operating mode/program by means of icons 25 that indicate whether the device is to be used in a "toning" mode (in which the muscle is manipulated during the treatment) or a "lines/wrinkles" mode (in which the electrodes are merely brushed over the skin's surface). Further icons 27 are provided to indicate which program has been selected for the chosen mode indicated by icons 25. Lastly, the screen 19 displays an indication 29 of the time remaining for a given treatment.

Figure 4:
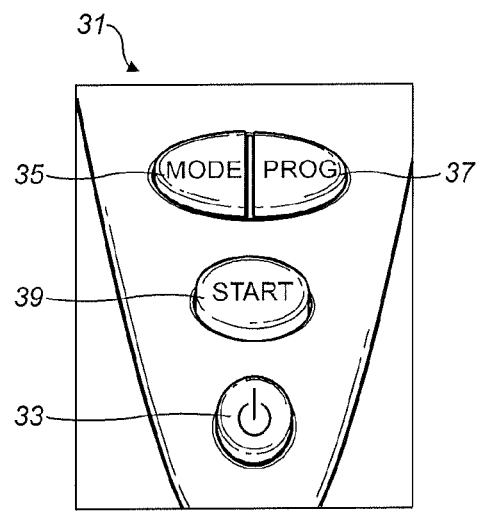
FIG. 4 is a schematic representation of a user interface of the device.

The first housing part 7 is also provided with a control panel 31 that has a plurality of buttons (or other user operable input devices) that can be operated to control the way in which the device 1 functions. Referring to FIG. 4, the control panel 31 includes an on/off switch 33 to switch the device on and off, a mode select button 35 to switch the device between the "toning" and "lines/wrinkles" modes and a "prog" button 37 to select a desired program for the selected mode (in this instance there being three different programs available for each mode). Finally, the control panel 31 includes a start button 39 that when pressed starts a selected program.

In one example, the device 1 is configured so that the "toning" (i.e. muscle lifting) mode subjects the skin and underlying muscle of the user to a lower frequency electrical stimulus than the "lines/wrinkles" operating mode. In addition, in one example, the device may use an alternating polarity square wave signal for the toning mode and a fixed polarity sine wave signal for the lines/wrinkles mode. By fixed polarity we mean that current flows in one direction from one electrode to the other, and by alternating polarity we mean that the current flows firstly in one direction between the electrodes, following which the polarity is reversed and the current flows back in the opposite direction.

In the lines/wrinkles mode the electrodes are merely brushed over the skin to effect a surface treatment of the user's skin and in this operating mode the locking means (when provided) may be operated to lock the first and second housing parts 7, 9 together. In the toning mode, however, the skin and underlying muscle of the user is manipulated whilst the treatment is ongoing, for example by squeezing the skin and muscle between the electrodes 15, or by using the electrodes to stretch the skin and muscle of the user.

An example of three programs for the two operating modes is shown in the table below.

| Program | Toning Mode | Lines/Wrinkles Mode |
| --- | --- | --- |
| 1 | 0.9 Hz; 150 uA square wave, alternating polarity | 500 Hz, 150 uA sine wave, fixed polarity |
| 2 | 0.7 Hz 300 uA square wave, alternating polarity | 500 Hz, 300 uA sine wave, fixed polarity |

-continued

| Program | Toning Mode | Lines/Wrinkles Mode |
|---|---|---|
| 3 | 0.3 Hz 600 uA square wave, alternating polarity | 500 Hz, 600 uA sine wave, fixed polarity |

Figure 7:
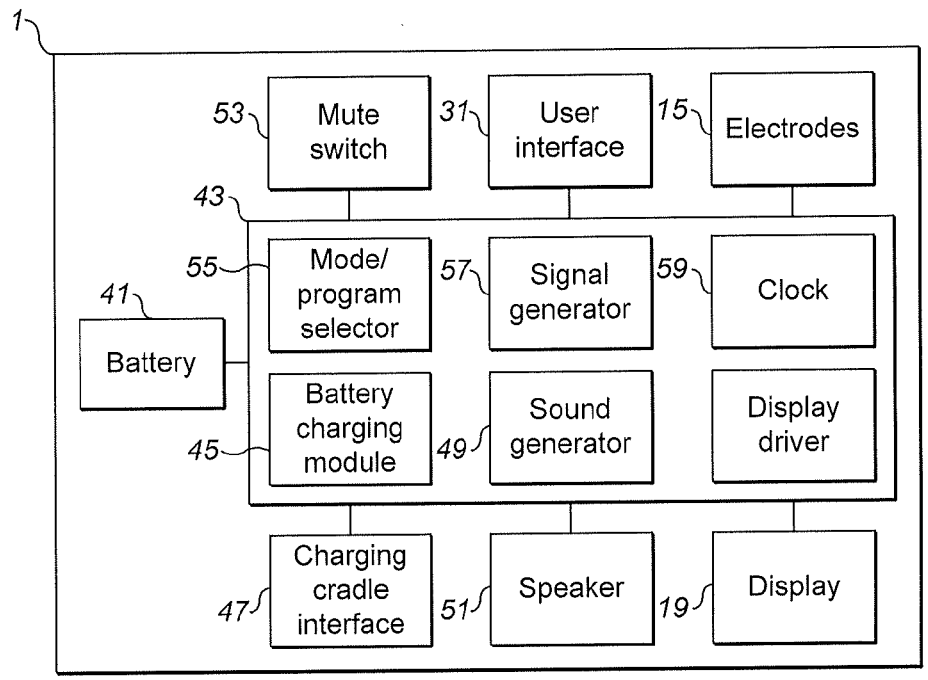
FIG. 7 is a block diagram showing electrical components of the device.

Referring now to FIG. 7 the device 1 includes a battery 41 that is preferably rechargeable by means of the charging cradle 3. The device 1 also includes a controller 43 (for example a processor) that incorporates a battery charging module 45 which controls the recharging of battery 41 via a charging cradle interface 47 which electrically connects to contacts in the charging cradle 3 when the device 1 is docked in the cradle.

The controller 43 includes a sound generator module 49 to generate sounds output by a speaker 51. The speaker 51 may output audible beeps whilst the device is being operated to stimulate a muscle. For example, the speaker 51 may output a short beep each second during operation of the device 1 followed by a longer beep after five seconds to indicate that treatment for that particular muscle has been completed. When operating in the toning mode, the speaker 51 may emit a short beep every second and then a long beep on the 6th second to signal to the user that they should move the device to a new muscle—the long beep only ceasing when contact with the skin is broken. When the device 1 is used in the lines/wrinkles mode the speaker 51 may emit a higher pitched beep every half second and then emit a long beep after 30 seconds to signal to the user to move onto another area of the face. Since audio beeps may sometimes be unnecessary or annoying, the device 1 may be provided with a mute switch 53 that when actuated will cause the controller 43 to turn off the sound generator module 49.

The controller 43 includes a mode/program selector module 55 that is responsive to the mode button 35 and program button 37 of the user interface 31 to select a desired operating mode and program. The controller 43 further comprises a signal generator 57 that is configured to generate an electrical signal in accordance with a selected mode/program for application to the electrodes 15. The controller 43 further comprises a clock module 59 that generates timing signals which are used by the controller to control the duration of any given program.

The controller 43 may be embodied by means of a processor running appropriate software, or by means of one or more application specific integrated circuits and/or other hard wired circuitry.

Because the first and second housing parts 7, 9 can move relative to one another, the user is able to manipulate the skin and underlying muscle by means of a device that can readily be used with one hand. For example, the user can manipulate the skin and tissue by squeezing it between the electrodes 15 or by using the electrodes to stretch the skin and muscle. When a user of the device 1 wishes to manipulate skin tissue by using the electrodes 15 to compress a muscle, the first and second housing parts can be moved apart from the rest condition shown in FIG. 5 and biasing members 18 will act to return the ends 14 towards the position shown in FIG. 5 and, as such, assist the user in compressing the muscle between the electrodes 15. When the user wishes to manipulate the skin to stretch a muscle, the device can be held in the fully closed position shown in FIG. 1, the electrodes 15 pressed against the skin and then the hold on the housing 5 relaxed to allow the biasing members 18 to urge the ends 14 of the first and second housing parts 7, 9 apart, thereby stretching the skin (and underlying muscle) against which the electrodes bear.

Thus the biasing members 18 assist the user in manipulating the skin and muscle to which an electrical current is to be applied. This is particularly advantageous given that, as aforementioned, the skin and muscle should be manipulated whilst being electrically stimulated if the muscle is to retain its re-educated form for longer.

The device 1 can also be used to apply an electric current to the skin surface by brushing the electrodes 15 over the skin's surface.

Figures 8, 9:
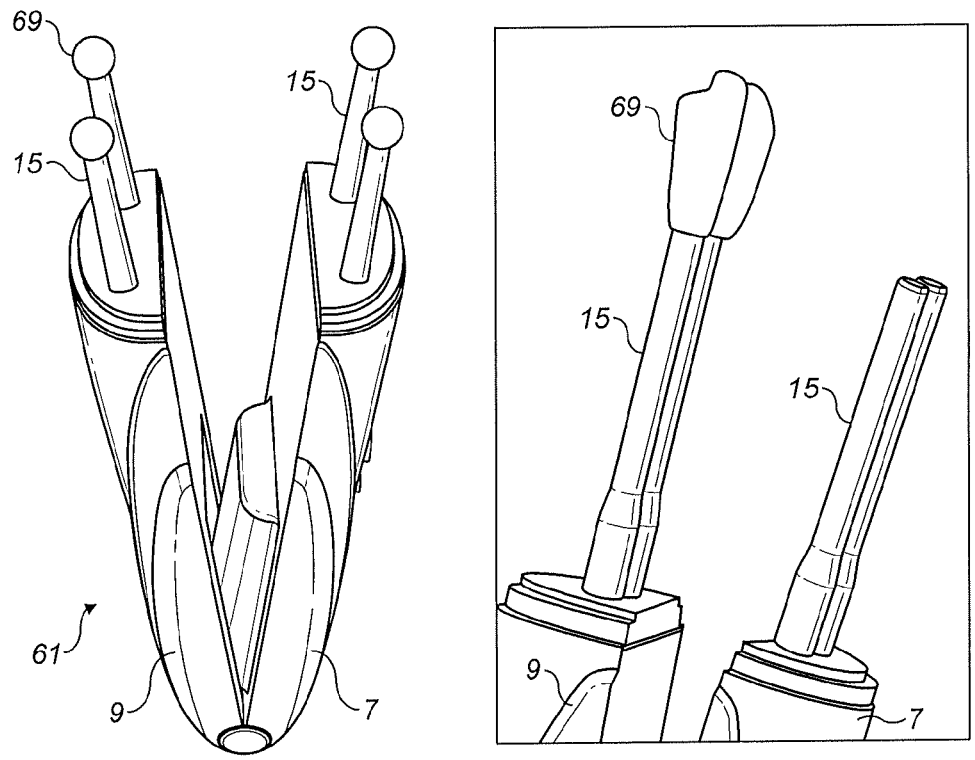
FIG. 8 is a schematic representation of a second example of a hand held electrostimulation device.
FIG. 9 shows electrodes of the device shown in FIG. 8.

FIG. 8 shows another electrostimulation device 61. The device 61 includes many components that are the same as or similar to those of the device 1. In the drawings, such components have been assigned the same reference numerals and to avoid unnecessary repetition of description may not be described again. The device 61 is configured to enable the spacing between the electrodes 15 carried by the first and second housing parts 7, 9 to be varied in the same way as the device 1.

Figure 10:
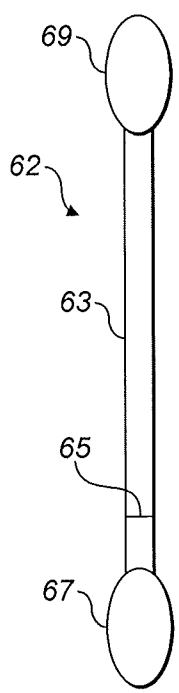
FIG. 10 is a schematic representation of a fluid-filled swab for use with the device of FIG. 8.

The electrodes 15 of the device 61 are configured for use with fluid bearing applicators, such as the cotton buds described in U.S. Pat. No. 5,702,035—i.e. cotton buds that carry or contain a fluid within them. As shown in FIG. 10 (and as described in U.S. Pat. No. 5,702,035), such cotton buds 62 comprise a tube 63 that carries a measure of fluid (such as a serum, medicament or beauty treatment) and is circumferentially scored to form a break line 65. The ends of the tube 63 are provided with respective cotton bud applicators 67, 69 of the type used for conventional cotton buds (for example, the Q-Tip™ brand of cotton buds). In use the tube 63 is broken at the break line 65, whereupon the fluid within the tube is drawn to the cotton bud applicator 69 distal from the break line 65 for application to the skin of the user.

The electrodes 15 of the device 61 are able to act as a support for a fluid-bearing cotton bud 62 to enable fluid to be dispensed onto the skin of the user whilst an electric current (preferably a microcurrent) is applied thereto). FIG. 8 shows the electrostimulation device 61 with each of the four electrodes 15 loaded with a cotton bud 62 and FIG. 9 shows the device with only two of the four electrodes loaded.

Figure 11:
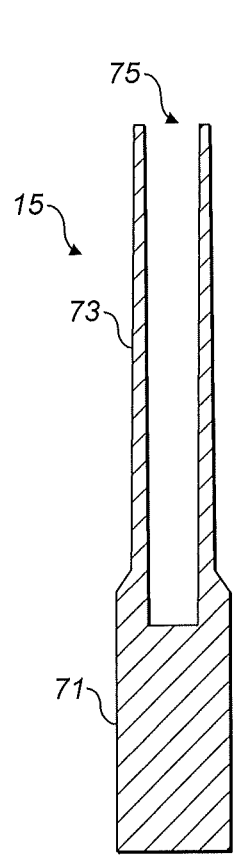
FIG. 11 is a schematic cross-sectional view through an electrode of the device shown in FIG. 8.
Figure 12:
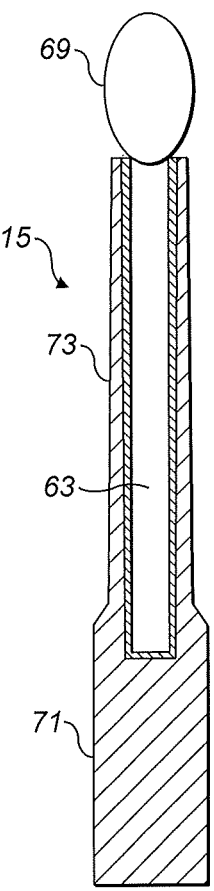
FIG. 12 is a schematic cross-sectional view of a swab such as that shown in FIG. 10 installed in an electrode as shown in FIG. 11.

As shown in FIGS. 11 and 12, the electrodes 15 of the device 61 each comprise a base part 71 that is coupled to the respective housing parts 7, 9 and a section 73 that projects from the base part. The section 73 defines a cavity 75 that is sized so that the tube 63 of a fluid bearing cotton bud 62 (or indeed any other similarly sized swab, fluid-bearing or otherwise) may be friction fitted and retained within the cavity 75 (as shown in FIG. 12). Once fitted within the cavities 75, the cotton buds 62 are able to deliver their fluid content directly to the particular part of the skin to which the current is being applied, and thus create much less mess than other previously proposed arrangements. The cotton buds can quickly and easily be changed when exhausted and the device itself can quickly and easily be cleaned. Furthermore, as an electrical microcurrent is supplied to the skin via the cotton applicators 69 of the cotton buds 62, the device can be used to perform for iontophoresis.

It should be understood that the electrostimulation device 61 may be configured to use other forms of fluid delivery applicator. For example the fluid delivery applicator may comprise a pad made of cotton or other material provided at either end of a tube that carries a fluid. It should also be noted that the term "cotton bud" is not intended to refer to any one particular brand of applicator.

In the examples illustrated by FIGS. 1 to 12, the first and second housing parts 7, 9 pivot with respect to one another to vary the distance between the electrodes 15. This is not essential as the housing parts may move relative to one another in other ways. For example, the housing parts may be configured to vary the distance between the electrodes by a relative sliding or rotational movement of the first and second housing parts. Still further ways in which the housing parts may move relative to one another to vary the distance between the electrodes will be described below with reference to FIGS. 13 to 16.

In the examples illustrated by FIGS. 1 to 12, the biasing members 18 are torsion springs that are disposed about the pivot axis defined by the hinge 11. Other forms of biasing member may be used and there may be just one biasing member or more than two. The biasing member(s) may, for example, be suitably positioned compression or tension springs, or suitably positioned members, such as blocks or pads, made of a resilient material such as an elastomer.

In the example illustrated in FIG. 6, the locking mechanism comprises a projection 50 engageable with in a recess 52. Examples of other suitable forms of locking mechanism include a detachable clip or ring that can be fitted in engagement with a suitable a suitable formation(s), such as recess(es) provided on or in the housing 5. Such a clip or ring may fit to the housing by, for example, snap-fitting. Another example is a hinged latch arm provided on one housing part that can be latch into a suitable recess provided on the other housing part.

The examples illustrated by FIGS. 1 to 12, comprise a rechargeable battery that is sealed within one of the housing part 7. However, non-rechargeable batteries can be used, in which case one of the housing parts would be provided with a user accessible battery compartment. Another alternative would be for the device to be powered by an external electrical power supply, in which case the device may be supplied with a cable with and an external transformer for transforming a mains electrical power supply into a supply suitable for use by the device.

Figure 13:
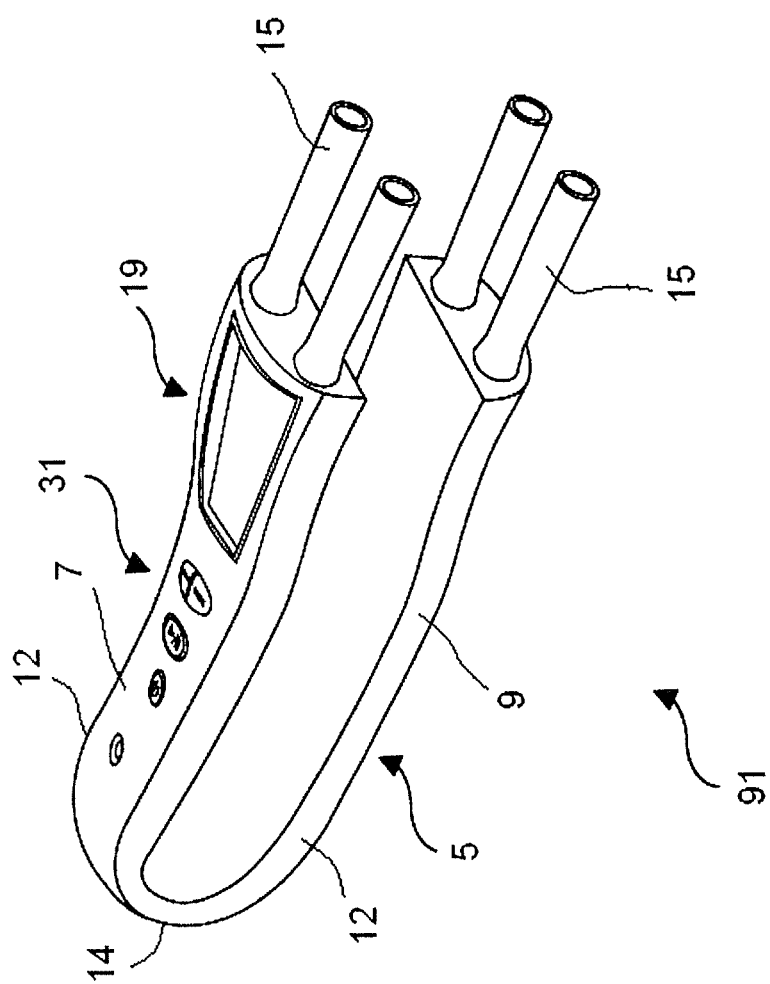
FIG. 13 is a perspective view of a third example of a hand held electrostimulation device.

FIG. 13 shows another hand held electrostimulation device 91. The device 91 includes components that are the same as, or similar to, those of the hand held electrostimulation devices 1, 61. In FIG. 13, such components have been assigned the same reference numerals and to avoid unnecessary repetition of description may not be described again.

The hand held electrostimulation device 91 comprises a handle 5 that is configured to fit in the hand of a normal adult user for one-handed operation. The handle 5 comprises a first side member 7 and a second side member 9. The first and second side members 7, 9 each have a free end from which at least one electrode 15 projects. The opposite ends 12 of the side members 7, 9 are linked by an arcuate member 14. The configuration of the side members 7, 9 and arcuate member 14 is such that the handle 5 has a generally U-shaped profile. In the illustrated example, each side member 7, 9 carries two electrodes, although, in other examples there may be just one electrode or more than two electrodes provided on each side member. The electrodes 15 may be solid or configured for use with fluid bearing applicators, for example, as disclosed with reference to FIGS. 8 to 12.

The hand held electrostimulation device 91 may have a display screen 19, which may, for example, be the same as or similar to the display screen described with reference to FIGS. 1 and 3. The device 91 may also be provided with a control panel 31, which may, for example be the same as or similar to the control panel described with reference to FIGS. 1 and 4. The device 91 may also be provided with a controller, which may be the same as, or similar to, the controller 43 described above with reference to FIG. 7.

The hand held electrostimulation device 91 may be battery powered. The handle 5 may be provided with a compartment (not shown) to house a battery(ies), which may be one-time use or rechargeable. Alternatively, the handle 5 may carry a sealed in battery that is rechargeable via a charging plug/socket arrangement or by non-contact charging, for example by inductive charging. Examples that have a battery(ies) rechargeable via a plug/socket arrangement may include an electrical connector configured to engage an electrical connector provided in a cradle such as the cradle 3 shown in FIG. 1.

The handle 5 may be a one-piece component made of a suitable plastics or polymer material. The handle may, for example be formed by molding. The handle 5 is configured such that a user can one-handedly cause relative movement of the first and second side members 7, 9 while holding the electrodes 15 against their skin. The handle 15 is resiliently biased to a rest position so that when the user relaxes the force that has been applied to the handle to move the first and second side members 7, 9 to from the rest position, the side members, and so the electrodes 15, are moved back towards the rest position. In some examples, one or more biasing elements may be provided to provide the resilient bias. For example, as illustrated by FIG. 14, a biasing element 93 may be provided. The biasing element 93 may be a plate, or leaf, spring having a curvature at least substantially corresponding to the curvature of the arcuate member 14. The biasing element 93 may be disposed within the handle 5 as shown in FIG. 14 or fitted to an inner or outer surface of the handle, for example by embedding in a recess defined by the handle. In other examples, as illustrated by FIG. 15, a biasing element 95 may extend between the side members 7, 9. The biasing element(s) 95 may be a compression or tension spring(s) according to the desired functionality. In some examples, it may not be necessary to provide a biasing element(s) to provide the resilient bias. Instead, the functionality of the biasing element(s) may be provided by the resilience of the material from which the handle 5 is made. In some examples, the resilient bias may be provided by the handle material in combination with one or more biasing elements.

The hand held electrostimulation device 91 may be operated in the same, or a similar, fashion to the hand held electrostimulation devices 1, 61 as described above and so to avoid unnecessary repetition of description, a detailed description of the device 91 is not provided here.

Figure 16:
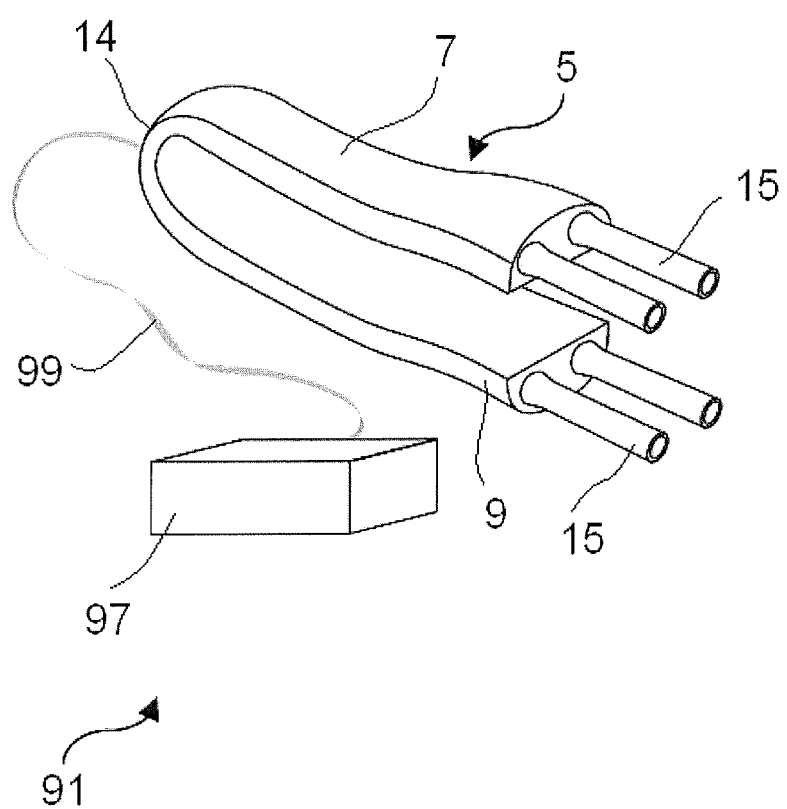
FIG. 16 is a perspective view of a fourth example of a hand held electrostimulation device.

FIG. 16 shows modifications that may be made to the hand held electrostimulation device 91. In this example, the controller, control panel, display screen and power supply are all omitted from the handle 5 and incorporated in one or more housings 97 that may be connected with the handle by one or more flexible electrical conductors, or leads, 99. The connection may be made using plugs and sockets, or may be permanent. It will be understood it is not essential that all of the controller, control panel, display screen and power supply are omitted from the handle and that one or more may be provided on the handle. For example, it may be convenient to have a display or input control functionality provided on the handle, while having the controller and power supply provided separately in a housing(s) 97.

In other examples, a hand held electrostimulation device having a handle similar to the handles shown in FIGS. 13 and 16 may have respective side members connected to a line by respective pivot connections at their inner ends.

The illustrated examples provide a hand held electrostimulation device by means of which a user can conveniently adjust the spacing of the electrodes and thereby grip or stretch a muscle in the course of a muscle toning treatment using just one hand and without the aid of a mirror or the like. In some examples, the muscle is manipulated by relative movement of the electrodes while they are in direct contact with the skin, while in other examples, the manipulation may be via fluid applicators held by the electrodes. In each case, muscle manipulation is achievable by one-handed operation while electricity from the electrodes is applied to the skin. The illustrated devices can also be used for a lines/wrinkle treatment where the electrodes are brushed over the surface of the user's skin.

The hand held electrostimulation devices 61, 91 allow the use of a fluid bearing applicator to deliver its fluid content directly to the particular part of the skin to which the current is being applied, and thus create much less mess than is the case with known devices and procedures. The fluid bearing applicator, such as the illustrated cotton bud can quickly and easily be changed when exhausted and after use, the device itself can quickly and easily be cleaned. Furthermore, examples of the device that allow the electrical current to be supplied to the skin via a fluid bearing applicator are particularly well-suited for iontophoresis.

Thus, although there have been described particular embodiments of the present invention of a new and useful Electrostimulation Devices it is not intended that such references be construed as limitations upon the scope of this invention except as set forth in the following claims.

What is claimed is:

1. A hand held electrostimulation skin massage device comprising:
    a handle comprising a first side member and a second side member, said handle having a length defining a lengthways direction of the skin massage device;
    at least one first electrode provided on said first side member, said at least one first electrode having a free end; and
    at least one second electrode provided on said second side member, said at least one second electrode having a free end,
    wherein said first and second side members each have a free end, said at least one first electrode extends beyond said free end of said first side member in said lengthways direction and said at least one second electrode extends beyond said free end of said second side member in said lengthways direction, and
    wherein said first and second electrodes are spaced apart and said handle is configured such that a user's hand can cause relative movement of said first and second side members from a rest position and is resiliently biased to return said first and second side members to said rest position to cause relative movement of said first and second electrodes to adjust said spacing between said first and second electrodes to a provide skin massage while applying electricity to said skin via said free ends of said first and second electrodes.

2. A device as claimed in claim 1, wherein said first and second side members have respective inner ends that are connected by an arcuate connection member.

3. A device as claimed in claim 2, wherein said handle is generally U-shaped.

4. A device as claimed in claim 1, wherein said first and second side members have respective inner ends, said first and second side members are linked at said inner ends and said relative movement of said first and second side members is centered in a portion of said handle disposed between said inner ends.

5. A device as claimed in claim 1, wherein said first and second side members are movable from said rest position to increase said spacing between said first and second electrodes and said resilient bias is configured to return said first and second housing parts to said rest position.

6. A device as claimed in claim 1, wherein said first and second side members are movable from said rest position to decrease said spacing between said first and second electrodes and said resilient bias is configured to return said first and second housing parts to said rest position.

7. A device as claimed in claim 1, wherein said handle comprises at least a handle portion made of a resilient material configured to provide said resilient bias.

8. A device as claimed in claim 7, wherein said handle portion is disposed between said first and second side members.

9. A device as claimed in claim 1, wherein said handle is a one-piece member.

10. A hand held electrostimulation skin massage device comprising:
    a handle comprising a first side member and a second side member;
    at least one first electrode provided on said first side member, said at least one first electrode having a free end;
    at least one second electrode provided on said second side member, said at least one second electrode having a free end; and
    at least one holder for a fluid-bearing applicator to hold a said applicator so as to enable fluid from said applicator to be applied to skin to which electricity is supplied via said electrodes,
    wherein said first and second side members each have a free end, said at least one first electrode extends from said free end of said first side member and said at least one second electrode extends from said free end of said second side member, and
    wherein said first and second electrodes are spaced apart and said handle is configured such that a user's hand can cause relative movement of said first and second side members from a rest position and is resiliently biased to return said first and second side members to said rest position to cause relative movement of said first and second electrodes to adjust said spacing between said first and second electrodes to a provide skin massage while applying electricity to said skin via said free ends of said first and second electrodes.

11. A device as claimed in claim 10, wherein said at least one said holder comprises a cavity defined by a said electrode.

12. A device as claimed in claim 11, wherein electricity from said electrodes is applied to said skin via a said fluid bearing applicator held in said at least one holder.

13. A device as claimed in claim 10, comprising a said fluid-bearing applicator friction-fitted in said at least one holder.

14. A device as claimed in claim 13, wherein said fluid-bearing applicator carries a cosmetic or therapeutic fluid.

15. A hand held electrostimulation skin massage device comprising:
    a handle comprising a first side member and a second side member;
    at least one first electrode provided on said first side member, said at least one first electrode having a free end;
    at least one second electrode provided on said second side member, said at least one second electrode having a free end; and
    at least one resilient biasing element connected with said handle,
    wherein said first and second side members each have a free end, said at least one first electrode extends from said free end of said first side member and said at least one second electrode extends from said free end of said second side member, and wherein said first and second electrodes are spaced apart and said handle is configured such that a user's hand can cause relative movement of said first and second side members from a rest position and is resiliently biased by said at least one resilient biasing element to return said first and second side members to said rest position to cause relative movement of said first and second electrodes to adjust said spacing between said first and second electrodes to a provide skin massage while applying electricity to said skin via said free ends of said first and second electrode.

16. A hand held electrostimulation skin massage device comprising:
a handle comprising a first side member and a second side member connected with said first side member to permit relative movement between said side members;
at least one first electrode carried by said first side member, said at least one first electrode having a free end;
at least one second electrode carried by said second side member, said at least second electrode having a free end; and
at least one biasing member to bias said first and second side members to a predetermined rest position that defines a spacing between said at least one first electrode and said at least one second electrode,
wherein said handle has a length defining a lengthways direction of the handle and each said side member has an inner side, an outer side disposed opposite said inner side and a free end extending between said inner and outer sides,
wherein said at least one first electrode projects beyond said free end of said first side member in said lengthways direction and said at least one second electrode projects beyond said free end of said second side member in said lengthways direction, and
wherein said handle is configured such that a user can change said spacing by one-handed manipulation of said handle to cause relative movement of said first and second side members against said at least one biasing member and said at least one biasing member operates to return said first and second side members to said rest position to simultaneously massage and apply electricity through said free ends of said first and second electrodes to skin of said user with which said free ends of said first and second electrodes are engaged.

17. An electrostimulation skin massage device comprising:
a hand held housing comprising a first side member and a second side member;
a first electrode carried by said first side member, said first electrode configured to hold a fluid applicator, said first electrode having a free end;
a second electrode carried by said second side member, said second electrode configured to hold a fluid applicator, said second electrode having a free end; and
a user operable control interface operable to couple a source of electricity to said electrodes,
wherein said handle is resiliently biased to a rest position at which a rest spacing between said first and second electrodes is defined,
wherein said handle is configured to permit a user to permit a user to hold said handle in one hand and manipulate said handle with said one hand to cause relative movement of said first and second side members against said resilient bias to change the spacing between said first and second electrodes, and
wherein said resilient bias is configured to return said handle to said rest position so that skin of said user which is engaged by respective fluid applicators projecting from said free ends of said first and second electrodes can be manipulated by relative movement of said first and second electrodes that is transmitted to said skin via said fluid applicators while electricity from said electrodes is applied to said skin via said fluid applicators.

18. A device as claimed in claim 17, further comprising at least one resilient biasing element connected with said handle to provide said resilient bias.

19. A device as claimed in claim 17, wherein said handle comprises at least a handle portion made of a resilient material configured to provide said resilient bias.

20. A device as claimed in claim 17, wherein said handle is a one-piece member.

21. A method of treatment of human skin using an electrostimulation skin massage device comprising a hand held housing comprising a first housing part and a second housing part that is connected with said first housing part such that said second housing part is movable relative to said first housing part, said method comprising:
applying a free end of a first electrode carried by said first housing part of said device and a free end of a second electrode carried by said second housing part of said device to said skin;
applying an electrical current to said skin via said free ends of said electrodes; and
manipulating said skin by relative movement of said first and second electrodes caused by relative movement of said first and second housing parts that causes a spacing between said first electrode and second electrode to change.

22. A method of treatment of human skin using an electrostimulation skin massage device comprising a hand held housing comprising a first housing part and a second housing part that is connected with said first housing part such that said second housing part is movable relative to said first housing part, said method comprising:
applying a first fluid applicator that projects from a free end of a first electrode carried by said first housing part of said device and a second fluid applicator that projects from a free end of a second electrode carried by said second housing part of said device to said skin;
applying an electrical current to said skin via said first and second fluid applicators; and
manipulating said skin by relative movement of said first and second electrodes caused by relative movement of said first and second housing parts that causes a spacing between said first electrode and second electrode to change.

* * * * *